(12) United States Patent
Krämer et al.

(10) Patent No.: US 9,656,983 B2
(45) Date of Patent: May 23, 2017

(54) PROCESS FOR STARTING UP A GAS PHASE OXIDATION REACTOR

(71) Applicant: BASF SE, Ludwigshafen (DE)

(72) Inventors: Michael Krämer, Katzweiler (DE); Nico F. Fischer, Heidelberg (DE); Jürgen Zühlke, Speyer (DE); Hans-Martin Allmann, Neunkirchen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/900,698

(22) PCT Filed: Jun. 16, 2014

(86) PCT No.: PCT/IB2014/062256
§ 371 (c)(1),
(2) Date: Dec. 22, 2015

(87) PCT Pub. No.: WO2014/207604
PCT Pub. Date: Dec. 31, 2014

(65) Prior Publication Data
US 2016/0152586 A1  Jun. 2, 2016

(30) Foreign Application Priority Data

Jun. 26, 2013 (EP) ..................... 13173691

(51) Int. Cl.
*C07D 307/89* (2006.01)
*C07C 51/265* (2006.01)
*C07C 51/31* (2006.01)

(52) U.S. Cl.
CPC .......... *C07D 307/89* (2013.01); *C07C 51/265* (2013.01); *C07C 51/313* (2013.01)

(58) Field of Classification Search
CPC .................................................. C07D 307/89
USPC ........................................................ 549/248
See application file for complete search history.

(56) References Cited

U.S. PATENT DOCUMENTS

| | | |
|---|---|---|
| 6,528,683 B1 | 3/2003 | Heidemann et al. |
| 6,700,000 B1 | 3/2004 | Heidemann et al. |
| 7,592,294 B2 | 9/2009 | Storck et al. |
| 7,615,513 B2 | 11/2009 | Guckel et al. |
| 7,851,398 B2 | 12/2010 | Neto et al. |
| 7,985,705 B2 | 7/2011 | Storck et al. |
| 8,106,220 B2 | 1/2012 | Mackewitz et al. |
| 8,492,566 B2 | 7/2013 | Wilmer et al. |
| 2003/0176715 A1 | 9/2003 | Reuter et al. |
| 2006/0235232 A1 | 10/2006 | Neto et al. |
| 2007/0135302 A1 | 6/2007 | Neto et al. |
| 2008/0200685 A1 | 8/2008 | Neto et al. |
| 2008/0312450 A1 | 12/2008 | Neto et al. |
| 2014/0018550 A1 | 1/2014 | Kramer et al. |
| 2014/0213801 A1 | 7/2014 | Altwasser et al. |

FOREIGN PATENT DOCUMENTS

| | | |
|---|---|---|
| DE | 22 12 947 A1 | 9/1973 |
| DE | 40 06 935 A1 | 9/1991 |
| DE | 19824532 A1 | 12/1999 |
| DE | 102005009473 A1 | 9/2006 |
| DE | 102005031465 A1 | 1/2007 |
| DE | 102010006854 A1 | 8/2011 |
| EP | 163 231 A1 | 12/1985 |
| EP | 831147 A2 | 3/1998 |
| EP | 1084115 A1 | 3/2001 |
| EP | 1670741 A1 | 6/2006 |
| EP | 2024351 A1 | 2/2009 |
| EP | 2027102 A2 | 2/2009 |
| EP | 2280921 A1 | 2/2011 |
| EP | 25 46 268 A1 | 1/2013 |
| WO | WO-9961433 A1 | 12/1999 |
| WO | WO-0216300 A1 | 2/2002 |
| WO | WO-2004103561 A1 | 12/2004 |
| WO | WO-2005/011862 A1 | 2/2005 |
| WO | WO-2005/030388 A1 | 4/2005 |
| WO | WO-2005030692 A1 | 4/2005 |
| WO | WO-2006/053732 A1 | 5/2006 |
| WO | WO-2006/131480 A1 | 12/2006 |
| WO | WO-2007003662 A1 | 1/2007 |
| WO | WO-2007135102 A2 | 11/2007 |
| WO | WO-2007135104 A1 | 11/2007 |
| WO | WO-2009124946 A1 | 10/2009 |
| WO | WO-2011/061132 A1 | 5/2011 |
| WO | WO-2011/128814 A1 | 10/2011 |

OTHER PUBLICATIONS

Krajewski et al., "Kinetics of the Vapor-Phase Oxidation of o-Xylene Over a Vanadium Oxide Catalyst", React. Kinet. Catal. Lett., vol. 6, No. 4, pp. 461-466 (1977).
Bo et al., Analysis on the Stability of Catalyst for o-Xylene Oxidation to Phthalic Anhydride Petrochemical Technology, vol. 5, pp. 421-423 (2004). English Abstract.
U.S. Appl. No. 14/900,663, Fischer et al.
International Search Report for PCT/IB2014/062256 mailed Feb. 26, 2015.

*Primary Examiner* — Taofiq A Solola
(74) *Attorney, Agent, or Firm* — Drinker Biddle & Reath LLP

(57) ABSTRACT

A process for preparing carboxylic acids and/or carboxylic anhydrides by gas phase oxidation of aromatic hydrocarbons, in which a gas stream comprising at least one aromatic hydrocarbon and molecular oxygen is passed continuously over a catalyst thermostatted by a heat carrier medium, which comprises keeping the temperature of the heat carrier medium constant during the startup of the reactor for at least 24 hours, during which neither the loading of the gas stream with hydrocarbons nor the gas stream volume is increased by more than 3%.

7 Claims, No Drawings

PROCESS FOR STARTING UP A GAS PHASE OXIDATION REACTOR

CROSS-REFERENCE TO RELATED APPLICATIONS

This application is a national stage application (under 35 U.S.C. §371) of PCT/IB2014/062256, filed Jun. 16, 2014, which claims benefit of European Application No. 13173691.0, filed Jun. 26, 2013, both of which are incorporated herein by reference in their entirety.

The present invention relates to a process for preparing carboxylic acids and/or carboxylic anhydrides by gas phase oxidation of aromatic hydrocarbons.

A multitude of carboxylic acids and/or carboxylic anhydrides is prepared industrially by the catalytic gas phase oxidation of hydrocarbons such as benzene, the xylenes, naphthalene, toluene or durene in fixed bed reactors. In this way it is possible to obtain, for example, benzoic acid, maleic anhydride, phthalic anhydride (PA), isophthalic acid, terephthalic acid or pyromellitic anhydride. In general, a mixture of an oxygenous gas and the starting material to be oxidized is passed through a reactor having a multitude of tubes in which a bed of a catalyst is present. For temperature regulation, the tubes are generally surrounded by a heat carrier medium, for example a salt melt.

In spite of this thermostatting, because of the high exothermicity of the reactions, what are called "hotspots" may develop within the catalyst bed, in which the temperature is significantly higher than in the rest of the bed. These "hotspots" cause unwanted side reactions, for example the total oxidation of the starting material, or lead to the formation of unwanted by-products. In addition, there is the risk that the catalyst—depending on the temperature in the hotspot—will be irreversibly damaged.

To attenuate these hotspots, there has been a move in industry to arrange catalysts of different activity layer by layer in the catalyst bed. The catalysts may, for example, be arranged such that the less active catalyst comes into contact with the reaction mixture first, meaning that it is toward the gas inlet in the bed, whereas the more active catalyst is toward the gas outlet (EP163 231, EP25 46 268). DE10 2005 009 473 describes a multilayer catalyst for preparation of PA, in which the first catalyst layer toward the gas inlet side has a higher catalyst activity than the second catalyst layer. The activity of the layers which follow rises toward the gas outlet side, meaning that the third catalyst layer has a higher activity than the second. WO2006/053732 describes a catalyst structure in which the catalyst activity of the individual layers increases from the gas inlet side to the gas outlet side. Additionally described is the possibility that individual layers within these structures are interrupted by more active preliminary layers or intermediate layers. Activity structures in which the catalyst layer immediately on the gas inlet side (i.e. the first catalyst layer) is the least active layer, which is followed by a second, more active catalyst layer, which is followed in turn by a less active third catalyst layer (having an activity between that of the first layer and that of the second layer), and in which the activity of the catalyst layer(s) which possibly follow(s) rises again, are accordingly conceivable.

To put a catalyst on stream ("startup"), the catalyst bed is typically brought by external heating of the reactor to a temperature above the later operating temperature, The catalyst is generally preformed at this temperature in a gas stream generally comprising oxygen for several hours (for example WO2006/131480).

Preferably the reactor is heated at 100° C. with an airflow of 0.5 to 1 $M^3$ (STP)/h/tube. Between 100° C. and 250° C. the organic binder in the catalyst is likely to decompose (WO2005/11862) and more preferably the airflow per tube is increased in this temperature range. Thermal decomposition of the binder can be monitored by analysis of the reactor output stream with (as described in EP 1831147, EP 2024351 and EP 2027102) or without an after-reactor. The formerly usual diversion of the decomposition products to the environment after the reactor or after-reactor can be dropped to the benefit of environmental protection if an offgas treatment facility is in place. Possible embodiments of such offgas treatment are an offgas scrubber connected to a thermal or catalytic offgas incinerator, or a direct offgas incinerator. At temperatures above 250° C. up to the maximum temperature of 400° C., for example, the airflow per tube is lowered preferably to 0.1 to 1 $m^3$ (STP)/h/tube. The reactor is left at maximum temperature preferably for 12 to 48 hours, before the temperature is lowered to the actual starting temperature.

As soon as the actual oxidation reaction commences as a result of the introduction of the aromatic hydrocarbons into the gas stream, the reaction temperature is maintained by the severe exothermicity of the reaction and the external heating can be gradually reduced and ultimately switched off. However, the development of a severe hotspot hinders a rapid increase in the loading of the gas stream, since the catalyst is irreversibly damaged above a certain hotspot temperature. Therefore, the loading of the gas stream with the hydrocarbon to be oxidized is increased in small steps, while the temperature of the heat carrier medium is gradually reduced at the same time, in order to minimize the absolute level of the hotspot temperature.

The startup time is generally understood to be the period of time from the first contacting of a catalyst with the reactant until the attainment of an essentially steady production state. In general, the startup time should be not more than 10% of the lifetime of the catalyst, which may be in the region of several years (cf. WO2011/128814). According to EP2280921, the startup time is, for example, within a range from 2 to 8 weeks or longer for a PA catalyst.

Several startup procedures are known from the prior art. For instance, DE 22 12 947A describes a process for preparing PA, in which the salt bath is heated at the start to 370 to 410° C. and an amount of air of at least 1 $M^3$ (STP)/h with a loading of at least 33 g of o-xylene/$m^3$ (STP) is passed through a reactor tube, so as to develop a hotspot temperature of 450 to 465° C. in the first third of the bed.

DE 198 24 532 discloses a process for preparing PA, in which the loading of the gas stream has been raised from 40 g/$m^3$ (STP) to 80 g/$m^3$ (STP) of o-xylene at a constant flow rate of 4 $m^3$ (STP)/h over several days.

DE 10 2005 031 465 discloses a process in which the catalyst bed is started up between 360 and 450° C. with an air flow rate of 1 to 3.5 $m^3$ (STP)/h and a loading of o-xylene of 20 to 65 g/$m^3$ (STP). In the first 7 to 20% of the catalyst bed, a hotspot temperature of 360 to less than 450° C. is developed.

EP 22080921 describes a process for starting up a gas phase oxidation reactor for oxidation of o-xylene to phthalic anhydride over a multilayer catalyst, wherein the initial loading is at least 30 g/$m^3$ (STP) lower than the target loading and the initial temperature is at least 30° C. higher than the target temperature. The target loading is specified as 60 to 110 g/$m^3$ (STP) and the target temperature as 340 to 365° C.

DE 10 2010 006 854 describes a process in which the catalyst bed is first heated to 365 to 395° C. and contacted with an air stream of 0.5 to 5 $M^3$ (STP)/h, the air steam having a hydrocarbon loading of 10 to 110 $g/m^3$ (STP). A hotspot is formed in the last 10 to 25% of the catalyst bed.

In order to be able to utilize the full performance of a catalyst very rapidly, the startup time should be as short as possible. Beside the limitation of the increase in loading per unit time to restrict the hotspot temperature in the catalyst bed, however, the productivity (i.e. product produced/unit time) and the product quality even in the early stage of the startup time play an important role. The oxidation of, for example, o-xylene to PA is a consecutive reaction which proceeds via various intermediates, for example o-tolylaldehyde and phthalide (Krajewski et. al. React. Kinet. Catal. Lett., 1977. Vol. 6. pages 461 to 466). Like the reactant o-xylene, these intermediates have to be converted quantitatively in the course of the reaction. In the reactor outlet gas, the concentrations of o-xylene and phthalide of below 0.1 wt.-% are targeted.

According to DE 10 20120 006 854, a deterioration in the product quality through an increase in the reaction temperature can be counteracted, for example, by (a) increasing the thermal bed temperature or (b) by decreasing the amount of air for the same hydrocarbon loading. However, this is associated with a decline in the amount of product, since the selectivity falls in case (a) and a smaller amount of reactant is used and hence also converted in case (b).

The performance of the processes for preparing carboxylic acids and/or carboxylic anhydrides by gas phase oxidation of aromatic hydrocarbons is measured primarily by the yields obtained and by the purity thereof. For example, high-quality PA (cf. DE 10 2010 006 854 A1, WO 2011/128814 A1) features minimum contents both of underoxidation products (especially phthalide and naphthoquinone) and of unconverted o-xylene and naphthalene, since these substances can be separated from one another only with very great difficulty and adversely affect the color number of the final pure PA.

The influence of startup and shutdown processes on the stability of catalysts for the oxidation of o-xylene to PA in a model experiment was studied and described by H. Bo et al. in Petrochemical Technology 2004. Vol. 5, pages 421 to 423.

There is a constant need for improved processes for gas phase oxidations which enable a maximum conversion combined with high selectivity and product purity.

It was an object of the present invention to provide a process for preparing carboxylic acids and/or carboxylic anhydrides by gas phase oxidation of aromatic hydrocarbons, which enables access to products of maximum purity combined with high conversion and simultaneously high selectivity.

This object is achieved by a process for preparing carboxylic acids and/or carboxylic anhydrides by gas phase oxidation of aromatic hydrocarbons, in which the constant lowering of the reaction temperature is paused for a certain time with the same or virtually the same carbon loading and the same or virtually the same volume flow rate.

The invention thus provides a process for preparing carboxylic acids and/or carboxylic anhydrides by gas phase oxidation of aromatic hydrocarbons, in which a gas stream comprising at least one aromatic hydrocarbon and molecular oxygen is passed continuously over a catalyst thermostatted by a heat carrier medium, which comprises keeping the temperature of the heat carrier medium constant during the startup of the reactor for at least 24 hours, during which neither the loading of the gas stream with hydrocarbons nor the gas stream volume is increased by more than 3%.

In a preferred embodiment of the invention, in the period during which the temperature of the heat carrier medium is kept constant, the loading of the gas stream with hydrocarbons is increased by a maximum of 1.5%.

In a further preferred embodiment of the invention, the gas stream volume in the period during which the temperature of the heat carrier medium is kept constant is increased by a maximum of 2.5%.

In the preparation of carboxylic acids and/or carboxylic anhydrides by gas phase oxidation of aromatic hydrocarbons, the heat carrier medium surrounding the reactor on commencement of startup is typically heated to a temperature of 380 to 410° C., which is then gradually lowered to a temperature of 340 to 365° C., while the loading of the gas stream with hydrocarbons simultaneously rises from about 25 to 30 $g/m^3$ (STP) to about 70 to 120 $g/m^3$ (STP). The loading of the gas stream with hydrocarbons can be increased, for example, at a rate of 0.5 to 10 $g/m^3$ (STP) per day. In general, the starting temperature is at least 30° C. higher than the operating temperature, usually 35 to 50° C. higher than the operating temperature. Operating temperature is regarded as being the temperature of the heat carrier medium in the steady state, i.e. after the startup phase has ended, during the productive operation of the reactor. To compensate for declining catalyst activity, the temperature of the heat carrier medium can, however, be increased slightly in the long term in the operating state (by less than 10° C./year). Gradually lowering the temperature of the heat carrier medium is understood in the context of this invention to mean a measurable lowering of the temperature of the heat carrier medium by at least 0.1° C. per 24 hours. Keeping the temperature of the heat carrier medium constant is understood in the context of this invention to mean that the temperature of the heat carrier medium changes by less than 0.1° C. per 24 hours.

The gas stream volume used in the process according to the invention is guided by the reactor size and the residence time required for the respective reaction, and is typically in the range from 0.5 to 5 $M^3$ (STP)/h per reactor tube, preferably in the range from 2.5 to 4.2 $m^3$ (STP)/h.

The process according to the invention is suitable, for example, for gas phase oxidation of aromatic $C_6$ to $C_{10}$ hydrocarbons such as benzene, the xylenes, toluene, naphthalene or durene (1,2,4,5-tetramethylbenzene) to carboxylic acids and/or carboxylic anhydrides such as maleic anhydride, phthalic anhydride, benzoic acid and/or pyromellitic anhydride. The process is particularly suitable for preparation of phthalic anhydride from o-xylene and/or naphthalene. The gas phase reactions for preparation of phthalic anhydride are common knowledge and are described, for example, in WO 2004/103561 on page 6.

Useful catalysts for these oxidation reactions have been found to be what are called coated catalysts, in which the catalytically active material has been applied in the form of a shell on an inert support material such as steatite. The catalytically active constituents used in the catalytically active material of these coated catalysts are generally titanium dioxide and vanadium pentoxide. In addition, small amounts of a multitude of other oxidic compounds which influence the activity and selectivity of the catalyst as promoters may be present in the catalytically active material.

The inert support materials used may be virtually all prior art support materials, as used advantageously in the production of coated catalysts for the oxidation of aromatic hydrocarbons to aldehydes, carboxylic acids and/or carboxylic anhydrides, for example quartz ($SiO_2$), porcelain, magnesium oxide, tin dioxide, silicon carbide, rutile, alumina ($Al_2O_3$), aluminum silicate, steatite (magnesium silicate), zirconium silicate, cerium silicate or mixtures of these support materials. The catalyst supports can be used, for example, in the form of spheres, rings, tablets, spirals, tubes, extrudates or chippings. The dimensions of these catalyst supports typically correspond to those of catalyst supports used customarily for production of coated catalysts for the gas phase reactions of aromatic hydrocarbons. Preference is given to using steatite in the form of spheres having a diameter of 3 to 6 mm or of rings having an external diameter of 5 to 9 mm and a length of 3 to 8 mm and a wall thickness of 1 to 2 mm.

Catalysts suitable for the catalytic gas phase oxidation of o-xylene and/or naphthalene to PA comprise a catalytically active material which comprises at least vanadium oxide and titanium dioxide and can be applied to the support material in one or more shells. Different shells may differ in their composition.

Preferably, the catalytically active material, based on the total amount of the catalytically active material, comprises 1 to 40% by weight of vanadium oxide, calculated as $V_2O_5$, and 60 to 99% by weight of titanium dioxide, calculated as $TiO_2$. In preferred embodiments, the catalytically active material may additionally comprise up to 1% by weight of a cesium compound, calculated as Cs, up to 1% by weight of a phosphorus compound, calculated as P, and up to 10% by weight of antimony oxide, calculated as $Sb_2O_3$. All figures for the composition of the catalytically active material are based on the calcined state thereof, for example after calcination of the catalyst at 450° C. for one hour.

Typically, titanium dioxide in the anatase modification is used for catalytically active material. The titanium dioxide preferably has a BET surface area of 15 to 60 $m^2/g$, especially 15 to 45 $m^2/g$, more preferably 13 to 28 $m^2/g$. The titanium dioxide used may consist of a single titanium dioxide or a mixture of titanium dioxides. In the latter case, the value for the BET surface area is determined as the weighted mean of the contributions of the individual titanium dioxides. The titanium dioxide used consists, for example, advantageously of a mixture of a $TiO_2$ having a BET surface area of 5 to 15 $m^2/g$ and a $TiO_2$ having a BET surface area of 15 to 50 $m^2/g$.

Suitable vanadium sources are particularly vanadium pentoxide or ammoniummetavanadate. Suitable antimony sources are various antimony oxides, especially antimony trioxide. Vanadium and antimony may additionally also be used in the form of a vanadium antimonate compound (WO2011/061132). The vanadium antimonate incorporated in the active material of at least one layer can be prepared by reaction of any desired vanadium compounds and antimony compounds. Preference is given to the direct reaction of the oxides to give a mixed oxide or vanadium antimonate. The vanadium antimonate may have different molar ratios of vanadium to antimony, and may optionally also comprise further vanadium compounds or antimony compounds and be used in a mixture with further vanadium compounds or antimony compounds.

Useful phosphorus sources include especially phosphoric acid, phosphorous acid, hypophosphorous acid, ammonium phosphate or phosphoric esters, and in particular ammonium dihydrogenphosphate. Useful sources of cesium include the oxide or hydroxide or the salts which can be converted thermally to the oxide, such as carboxylates, especially the acetate, malonate or oxalate, carbonate, hydrogencarbonate, sulfate or nitrate.

As well as the optional additions of cesium and phosphorus, small amounts of a multitude of other oxidic compounds which influence the activity and selectivity of the catalyst as promoters, for example by lowering or increasing the activity thereof, may be present in the catalytically active material. Examples of such promoters include the alkali metals, more particularly (excluding cesium, which has been mentioned) lithium, potassium and rubidium, which are usually used in the form of their oxides or hydroxides, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide.

In addition, among the promoters mentioned, useful additives preferably also include the oxides of niobium and tungsten in amounts of 0.01 to 0.50% by weight, based on the catalytically active material.

The shell(s) of the coated catalysts are appropriately applied by spray application of a suspension of $TiO_2$ and $V_2O_5$, which optionally comprises sources of the abovementioned promoter elements, to the fluidized support (EP1670741, WO2005/030388). Before the coating, the suspension is preferably stirred for a sufficiently long period, for example 2 to 30 hours, especially 12 to 25 hours, to break up agglomerates of the suspended solids and to obtain a homogeneous suspension. The suspension typically has a solids content of 20 to 50% by weight. The suspension medium is generally aqueous, for example water itself or an aqueous mixture with a water-miscible organic solvent such as methanol, ethanol, isopropanol, formamide and the like.

In general, organic binders are added to the suspension, preferably copolymers, advantageously in the form of an aqueous dispersion, of acrylic acid/maleic acid, vinyl acetate/vinyl laurate, vinyl acetate/acrylate, styrene/acrylate and vinyl acetate/ethylene. The binders are commercially available as aqueous dispersions having a solids content of, for example, 35 to 65% by weight. The amount of such binder dispersions used is generally 2 to 45% by weight, preferably 5 to 35% by weight, more preferably 7 to 20% by weight, based on the weight of the suspension.

The support is fluidized in, for example, a fluidized bed apparatus in an ascending gas stream, especially air. The apparatuses usually consist of a conical or spherical vessel in which the fluidizing gas is introduced from the bottom or from the top through an immersed tube. The suspension is sprayed into the fluidized bed via nozzles from the top, at the side or from below. It is advantageous to use a riser tube arranged centrally or concentrically around the immersed tube. Within the riser tube, there is a higher gas velocity which transports the support particles upward. Within the outer ring, the gas velocity is only slightly above the fluidization velocity. Thus, the particles are moved vertically in a circular manner. A suitable fluidized bed apparatus is described, for example, in DE-A 4006935.

In the coating of the catalyst support with the catalytically active material, coating temperatures of 20 to 500° C. are generally employed, and the coating can be effected under atmospheric pressure or under reduced pressure. In general, the coating is effected at 0° C. to 200° C., preferably at 20 to 150° C., especially at 60 to 120° C.

The shell thickness of the catalytically active material is generally 0.02 to 0.2 mm, preferably 0.05 to 0.15 mm. The active material content in the catalyst is typically 5 to 25% by weight, usually 7 to 15% by weight.

As a result of thermal treatment of the precatalyst thus obtained at temperatures above 200 to 500° C., the binder escapes from the shell applied through thermal decomposition and/or combustion. Preference is given to effecting the thermal treatment in situ in the gas phase oxidation reactor.

It has been found to be particularly advantageous when a catalyst bed composed of various catalysts which differ in terms of their catalytic activity and/or chemical composition of the active material thereof, and which are introduced successively as layers in different zones of the reactor, is used. Preferably, when two reaction zones are employed, a catalyst used in the first reaction zone, i.e. that toward the inlet of the gas stream, is one which has a somewhat lower catalytic activity compared to the catalyst present in the second reaction zone, i.e. that toward the outlet of the gas stream. In general, the reaction is controlled through the temperature setting such that the majority of the aromatic hydrocarbons present in the gas stream is converted at maximum yield in the first zone. Preference is given to using three- to five-zone catalyst systems, especially three- and four-zone catalyst systems. A three-zone catalyst system for o-xylene oxidation to PA is described, for example, in EP 1084115.

Instead of mutually delimited zone of different catalysts, it is also possible to bring about a quasi-continuous transition of the zone and hence a quasi-homogeneous change in the active material composition or in the content thereof by inserting a zone with a mixture of the successive catalysts at the transition from one zone to the next zone.

The bed length of the first catalyst zone (CZL1) is preferably in the range from 10 to 50%, more preferably in the range from 15 to 30%, of the total catalyst fill height in the reactor. Typical reactors have a fill height of 250 cm to 400 cm. The catalyst zones may optionally also be distributed over several reactors.

The process according to the invention achieves a distinct improvement in the product quality, expressed in reduced contents of unconverted aromatic hydrocarbon, and also of underoxidation products, for example phthalide or naphthoquinone in the case of preparation of PA from o-xylene and/or naphthalene.

The process according to the invention can also be used in catalytic gas phase oxidations to improve the product quality.

The invention further provides for the use of the process described above for improving the product quality in the preparation of carboxylic acids and/or carboxylic anhydrides by gas phase oxidation of aromatic hydrocarbons.

The examples which follow illustrate the invention without limiting it.

Example A

Oxidation of o-xylene to Phthalic Anhydride

Preparation of the Catalyst Zones
Catalyst zone 1 (CZ1) (vanadium antimonate as V and Sb source):
Preparation of Vanadium Antimonate:
2284.1 g of vanadium pentoxide and 1462 g of antimony trioxide (Antraco ACC-BS, approx. 4% valentinite and 96% senarmontite; $Sb_2O_3 \geq 99.8\%$ by weight; As≤800 ppm by weight, Pb≤800 ppm by weight, Fe≤30 ppm by weight, mean particle size =1.4 μm) were suspended in 5.6l of demineralized water and the suspension was stirred under reflux for 15 hours. Thereafter, the suspension was cooled to 80° C. and dried by means of spray drying. The inlet temperature was 340° C., the exit temperature 110° C. The spray powder thus obtained had a BET surface area of 89 $m^2/g$ and had a vanadium content of 32% by weight and an antimony content of 30% by weight. The product had the following crystalline constituents: valentinite (ICPDS: 11-0689): approx. 3%; senarmontite (ICPDS: 43-1071): approx. 2%; vanadium antimonate (ICPDS: 81-1219): approx. 95%. The mean crystal size of the vanadium antimonate was approx. 9 nm.
Suspension Mixing and Coating:
2 kg of steatite rings (magnesium silicate) having dimensions of 7 mm×7 mm×4 mm were coated in a fluidized bed apparatus with 752 g of a suspension of 4.4 g of cesium carbonate, 413.3 g of titanium dioxide (Fuji TA 100 CT; anatase, BET surface area 27 $m^2/g$), 222.5 g of titanium dioxide (Fuji TA 100; anatase, BET surface area 7 $m^2/g$), 86.9 g of vanadium antimonate (as prepared above), 1870.1 g of demineralized water and 76.7 g of organic binder (copolymer of vinyl acetate and vinyl laurate in the form of a 50% by weight aqueous dispersion).

After calcination of the catalyst at 450° C. for one hour, the active material applied to the steatite rings was 8.3%. The analyzed composition of the active material consisted of 7.1% V205, 4.5% Sb203, 0.50% Cs, remainder $TiO_2$.

Catalyst zone 2 (CZ2) (vanadium pentoxide and antimony trioxide, respectively, as V and Sb sources):
2 kg of steatite rings (magnesium silicate) having dimensions of 7 mm×7 mm×4 mm were coated in a fluidized bed apparatus with 920 g of a suspension of 3.0 g of cesium carbonate, 446.9 g of titanium dioxide (Fuji TA 100 C; anatase, BET surface area 20 $m^2/g$), 133.5 g of titanium dioxide (Fuji TA 100; anatase, BET surface area 7 $m^2/g$), 45.4 g of vanadium pentoxide, 11.6 g of antimony trioxide, 1660.1 g of demineralized water and 104.5 g of organic binder (copolymer of vinyl acetate and vinyl laurate in the form of a 50% by weight aqueous dispersion).

After calcination of the catalyst at 450° C. for one hour, the active material applied to the steatite rings was 10.0%. The analyzed composition of the active material consisted of 7.1% $V_2O_5$, 1.8% $Sb_2O_3$ 0.38% Cs, remainder $TiO_2$.

Catalyst zone 3 (CZ3) (vanadium pentoxide and antimony trioxide, respectively, as V and Sb sources):
2 kg of steatite rings (magnesium silicate) having dimensions of 7 mm×7 mm×4 mm were coated in a fluidized bed apparatus with 750 g of a suspension of 2.33 g of cesium carbonate, 468.7 g of titanium dioxide (Fuji TA 100 C; anatase, BET surface area 20 $m^2/g$), 76.3 g of titanium dioxide (Fuji TA 100; anatase, BET surface area 7 $m^2/g$), 48.7 g of vanadium pentoxide, 16.7 g of antimony trioxide, 1588.0 g of demineralized water and 85.2 g of organic binder (copolymer of vinyl acetate and vinyl laurate in the form of a 50% by weight aqueous dispersion).

After calcination of the catalyst at 450° C. for one hour, the active material applied to the steatite rings was 8.5%. The analyzed composition of the active material consisted of 7.95% $V_2O_5$, 2.7% $Sb_2O_3$, 0.31% Cs, remainder $TiO_2$.

Catalyst Zone 4 (CZ4) (Vanadium Pentoxide and Antimony Trioxide, Respectively, as V and Sb Sources):
2 kg of steatite rings (magnesium silicate) having dimensions of 7 mm×7 mm×4 mm were coated in a fluidized bed apparatus with 760 g of a suspension of 1.7 g of cesium carbonate, 370.1 g of titanium dioxide (Fuji TA 100 CT; anatase, BET surface area 27 $m^2/g$), 158.6 g of titanium dioxide (Fuji TA 100; anatase, BET surface area 7 $m^2/g$), 67.3 g of vanadium pentoxide, 14.8 g of antimony trioxide, 1587.9 g of demineralized water and 86.3 g of organic binder (copolymer of vinyl acetate and vinyl laurate in the form of a 50% by weight aqueous dispersion).

After calcination of the catalyst at 450° C. for one hour, the active material applied to the steatite rings was 8.5%. The analyzed composition of the active material consisted of 11% $V_2O_5$, 2.4% Sb2O3, 0.22% Cs, remainder TiO2.

Catalyst zone 5 (CZ5) (vanadium pentoxide and antimony trioxide, respectively, as V and Sb sources):

2 kg of steatite rings (magnesium silicate) having dimensions of 7 mm×7 mm×4 mm were coated in a fluidized bed apparatus with 850 g of a suspension of 389.8 g of titanium dioxide (Fuji TA 100 CT; anatase, BET surface area 27 $m^2/g$), 97.5 g of titanium dioxide (Fuji TA 100; anatase, BET surface area 7 $m^2/g$), 122.4 g of vanadium pentoxide, 1587.9 g of demineralized water and 96.5 g of organic binder (copolymer of vinyl acetate and vinyl laurate in the form of a 50% by weight aqueous dispersion).

After calcination of the catalyst at 450° C. for one hour, the active material applied to the steatite rings was 9.1%. The analyzed composition of the active material consisted of 20% $V_2O_5$, 0.38% P, remainder $TiO_2$.

Example 1 (INVENTIVE)

Catalytic Oxidation of o-xylene to Phthalic Anhydride on the Industrial Scale

The catalytic oxidation of o-xylene to phthalic anhydride was performed on the industrial scale in a salt bath-cooled shell-and-tube reactor having a total of 18 900 tubes. From the reactor inlet to the reactor outlet, in each case 80 cm of CZ1, 60 cm of CZ2, 70 cm of CZ3, 50 cm of CZ4 and 60 cm of CZ5 were introduced into the individual tubes having an internal width of 25 mm. The catalyst layers, based on the above-described preparation of CZ1 to CZ5, were prepared in batches of in each case 150 kg of steatite rings. The iron tubes were surrounded by a salt melt for temperature regulation.

Preforming of the catalyst was effected under air at 400° C.

The catalyst was started up at 386° C. and the following gas streams were passed through the tubes from the top downward (calculated as flow rate per individual tube): air 3.0 to 4.0 $M^3$ (STP)/h of air with loadings of 98.8 to 99.4% by weight o-xylene of 30 to 100 g/$m^3$ (STP). The thermal bed temperature (salt bath temperature) was lowered proceeding from 386° C. and, at the same time, the loading of o-xylene was varied according to the table which follows. The PA yields were measured in the reactor outlet gas and are reported in % by mass (kg of PA per kg of o-xylene converted), based on 100% o-xylene.

| Run time [hours] | Salt bath temperature [° C.] | Gas stream volume [$m^3$ (STP)/h] | Loading [g of o-xylene/ $m^3$ (STP)] | o-Xylene in the reactor outlet gas [% by wt.] | Phthalide in the reactor outlet gas [% by wt.] |
|---|---|---|---|---|---|
| 24 | 386 | 3.0 | 35.0 | 0.002 | 0.009 |
| 48 | 382 | 3.25 | 37.0 | 0.002 | 0.008 |
| 72 | 380.1 | 3.5 | 38.5 | 0.003 | 0.009 |
| 96 | 378 | 3.75 | 40.0 | 0.004 | 0.021 |
| 120 | 376 | 3.8 | 40.5 | 0.003 | 0.009 |
| 144 | 374 | 3.8 | 43.5 | 0.004 | 0.014 |
| 168 | 373 | 3.8 | 45.0 | 0.004 | 0.014 |
| 192 | 372 | 3.85 | 46.0 | 0.014 | 0.031 |
| 216 | 371 | 3.88 | 47.0 | 0.004 | 0.019 |
| 240 | 370 | 3.83 | 48.0 | 0.005 | 0.022 |
| 264 | 369 | 3.83 | 49.0 | 0.007 | 0.022 |
| 288 | 368 | 3.83 | 50.0 | 0.007 | 0.025 |
| 312 | 367 | 3.83 | 51.0 | 0.007 | 0.026 |
| 336 | 366 | 3.83 | 53.6 | 0.008 | 0.028 |
| 360 | 365 | 3.83 | 54.8 | 0.007 | 0.031 |
| 384 | 363 | 3.83 | 56.6 | 0.009 | 0.035 |
| 408 | 361 | 3.83 | 57.4 | 0.010 | 0.041 |
| 432 | 359 | 3.83 | 59.2 | 0.014 | 0.062 |
| 456 | 358.5 | 3.83 | 60.9 | 0.026 | 0.059 |
| 480 | 357.5 | 3.83 | 62.7 | 0.030 | 0.064 |
| 504 | 356.6 | 3.85 | 63.7 | 0.031 | 0.066 |
| 528 | 355.5 | 3.85 | 65.0 | 0.043 | 0.083 |
| 552 | 354.5 | 3.85 | 66.0 | 0.068 | 0.102 |
| 576 | 354.4 | 3.85 | 67.0 | 0.088 | 0.123 |
| 600 | 354.4 | 3.85 | 67.1 | 0.079 | 0.100 |
| 624 | 354.4 | 3.85 | 68.0 | 0.060 | 0.092 |
| 648 | 353.9 | 3.85 | 69.3 | 0.067 | 0.100 |
| 672 | 353.9 | 3.85 | 70.0 | 0.060 | 0.090 |
| 696 | 353.4 | 3.88 | 71 | 0.069 | 0.098 |

It is apparent that the contents of o-xylene and phthalide, an underoxidation product, in the reactor outlet gas are reduced by pausing the lowering of the temperature (after 576 to 624 h or after 648 to 672 h), with a simultaneous slight increase in the loading of o-xylene in this case.

Example 2 (INVENTIVE)

Catalytic Oxidation of o-xylene to Phthalic Anhydride on the Pilot Tube Scale

The catalytic oxidation of o-xylene to phthalic anhydride was conducted in a salt bath-cooled tubular reactor having an internal diameter of the tubes of 25 mm. From the reactor inlet to the reactor outlet, in each case 80 cm of CZ1, 60 cm of CZ2, 70 cm of CZ3, 50 cm of CZ4 and 60 cm of CZ5 were introduced into an iron tube of length 3.5 m with an internal width of 25 mm, The iron tube was surrounded by a salt melt for temperature regulation; a 4 mm external diameter thermowell with installed tensile element served for catalyst temperature measurement.

Preforming of the catalysts was effected under 0.1 $M^3$ (STP)/h of air at 400° C. for about 38 hours.

After starting up the catalyst at 386° C., 3.0 to 4.0 $m^3$ (STP) of air per hour flowed through the tube from the top downward with loadings of 99-99.4% by weight o-xylene of 30 to 100 g/$m^3$ (STP). The thermal bed temperature (salt bath temperature) was lowered proceeding from 386° C. The PA yields were measured in the reaction outlet gas and are reported in % by mass (kg of PA per kg of o-xylene converted) based on 100% o-xylene.

The different operating parameters are summarized in the following table:

| Run time [hours] | Salt bath temperature [° C.] | Gas stream volume [$m^3$ (STP)/h] | Loading [g of o-xylene/ $m^3$ (STP)] | o-Xylene in the reactor outlet gas [% by wt.] | Phthalide in the reactor outlet gas [% by wt.] |
|---|---|---|---|---|---|
| 24 | 386 | 3.3 | 33 | n.d. | n.d. |
| 48 | 382 | 3.3 | 33 | n.d. | n.d. |
| 72 | 380 | 3.3 | 33 | 0.00 | 0.05 |
| 96 | 378 | 3.5 | 43 | 0.01 | 0.06 |
| 120 | 376 | 3.7 | 45 | 0.02 | 0.09 |

-continued

| Run time [hours] | Salt bath temperature [° C.] | Gas stream volume [m³ (STP)/h] | Loading [g of o-xylene/ m³ (STP)] | o-Xylene in the reactor outlet gas [% by wt.] | Phthalide in the reactor outlet gas [% by wt.] |
|---|---|---|---|---|---|
| 144 | 374 | 4.0 | 46 | 0.04 | 0.14 |
| 168 | 372 | 4.0 | 48 | 0.05 | 0.16 |
| 192 | 370 | 4.0 | 51 | n.d. | n.d. |
| 216 | 368 | 4.0 | 51 | n.d. | n.d. |
| 240 | 366 | 4.0 | 51 | n.d. | n.d. |
| 264 | 365 | 4.0 | 51 | 0.12 | 0.23 |
| 288 | 365 | 4.1 | 51 | 0.11 | 0.23 |
| 312 | 365 | 4.0 | 51 | 0.08 | 0.19 |
| 336 | 367 | 4.0 | 51 | 0.06 | 0.10 | n.d.: not determined

It is apparent that the contents of o-xylene and of phthalide, an underoxidation product, in the reactor outlet gas are reduced by pausing the lowering of the temperature (after 288 to 312 h), with a simultaneous slight increase in the volume flow rate in this case.

Examples 3 to 8 which follow were started up analogously to examples 1 and 2 at 386° C., and the salt bath temperature was lowered continuously until the operating points described had been attained.

Example 3 (INVENTIVE)

The different operating parameters are summarized in the following table:

| Run time [hours] | Salt bath temperature [° C.] | Gas stream volume [m³ (STP)/h] | Loading [g of o-xylene/m³ (STP)] | o-Xylene in the reactor outlet gas [% by wt.] | Phthalide in the reactor outlet gas [% by wt.] | PA yield [% by wt.] |
|---|---|---|---|---|---|---|
| 192 | 368 | 4 | 63 | 0.07 | 0.19 | 112.3 |
| 216 | 366 | 4 | 66 | 0.11 | 0.23 | 112.0 |
| 240 | 365 | 4 | 68 | 0.12 | 0.24 | 112.2 |
| 264 | 365 | 4 | 68 | 0.10 | 0.22 | 112.4 |
| 288 | 365 | 4 | 68 | 0.09 | 0.19 | 112.3 |

Example 4 (INVENTIVE)

The different operating parameters are summarized in the following table:

| Run time [days] | Salt bath temperature [° C.] | Gas stream volume [m³ (STP)/h] | Loading [g of o-xylene/m³ (STP)] | o-Xylene in the reactor outlet gas [% by wt.] | Phthalide in the reactor outlet gas [% by wt.] | PA yield [% by wt.] |
|---|---|---|---|---|---|---|
| 192 | 370 | 4.0 | 67 | 0.09 | 0.22 | 111.7 |
| 216 | 368 | 4.0 | 71 | 0.11 | 0.24 | 111.8 |
| 240 | 368 | 4.0 | 71 | 0.08 | 0.21 | 111.9 |

Pausing the lowering of the salt bath temperature in examples 3 and 4 led to an improvement in the product gas composition, while the other reaction parameters remained unchanged.

Example 5 (NONINVENTIVE)

The different operating parameters are summarized in the following table:

| Run time [days] | Salt bath temperature [° C.] | Gas stream volume [m³ (STP)/h] | Loading [g of o-xylene/m³ (STP)] | o-Xylene in the reactor outlet gas [% by wt.] | Phthalide in the reactor outlet gas [% by wt.] | PA yield [% by wt.] |
|---|---|---|---|---|---|---|
| 240 | 368 | 4.0 | 54 | 0.05 | 0.14 | 109.7 |
| 264 | 366 | 4.0 | 57 | 0.08 | 0.16 | 111.2 |
| 288 | 365 | 4.0 | 60 | 0.12 | 0.18 | 110.8 |
| 312 | 364 | 4.0 | 60 | n.d. | n.d. | n.d. |
| 336 | 363 | 4.0 | 62 | 0.13 | 0.19 | 110.5 |

-continued

| Run time [days] | Salt bath temperature [° C.] | Gas stream volume [m³ (STP)/h] | Loading [g of o-xylene/m³ (STP)] | o-Xylene in the reactor outlet gas [% by wt.] | Phthalide in the reactor outlet gas [% by wt.] | PA yield [% by wt.] |
|---|---|---|---|---|---|---|
| 360 | 362 | 4.0 | 64 | n.d. | n.d. | n.d. |
| 384 | 361.3 | 4.0 | 64 | n.d. | n.d. | n.d. |
| 408 | 360.6 | 4.0 | 64 | 0.14 | 0.21 | 112.0 | n.d.: not determined

Constantly lowering the salt bath temperature leads to a deterioration in the product gas composition.

Example 6 (NONINVENTIVE)

The different operating parameters are summarized in the following table:

| Run time [days] | Salt bath temperature [° C.] | Gas stream volume [m³ (STP)/h] | Loading [g of o-xylene/m³ (STP)] | o-Xylene in the reactor outlet gas [% by wt.] | Phthalide in the reactor outlet gas [% by wt.] | PA yield [% by wt.] |
|---|---|---|---|---|---|---|
| 192 | 370 | 4.0 | 64 | 0.08 | 0.25 | 111.5 |
| 216 | 368 | 4.0 | 67 | 0.11 | 0.26 | 112.2 |
| 240 | 366 | 4.0 | 70 | 0.12 | 0.28 | 112.1 |

Constantly lowering the salt bath temperature (combined with an increase in the loading of o-xylene) in examples 5 and 6 led to a deterioration in the product gas composition.

Example 7 (NONINVENTIVE)

The different operating parameters are summarized in the following table:

| Run time [days] | Salt bath temperature [° C.] | Gas stream volume [m³ (STP)/h] | Loading [g of o-xylene/m³ (STP)] | o-Xylene in the reactor outlet gas [% by wt.] | Phthalide in the reactor outlet gas [% by wt.] | PA yield [% by wt.] |
|---|---|---|---|---|---|---|
| 168 | 368 | 4 | 58.5 | 0.08 | 0.21 | 113.0 |
| 192 | 366 | 4 | 60.5 | 0.11 | 0.23 | 113.0 |
| 216 | 364 | 4 | 60.5 | 0.15 | 0.28 | 113.8 |
| 240 | 364 | 4 | 55.5 | 0.12 | 0.24 | 114.0 |
| 264 | 364 | 3.5 | 60.5 | 0.04 | 0.11 | 112.5 |

Continuous lowering even in the case of identical loading and gas stream volume (analyses after 192 and 216 h) leads to a deterioration in the product gas composition. By reducing the loading or the residence time, the product quality can be improved at the cost of productivity (analyses after 240 h and after 264 h).

Example B

Oxidation of Naphthalene or Mixtures of Naphthalene and o-xylene to Phthalic Anhydride Preparation of the Catalyst Zones
Catalyst Zone 1 (CZ1)
2 kg of steatite rings (magnesium silicate) in the form of rings having dimensions of 8 mm×6 mm×5 mm were coated in a fluidized bed apparatus with 860 g of a suspension of 6.92 g of cesium carbonate, 562.34 g of titanium dioxide (Fuji TA 100 C; anatase, BET surface area 20 m²/g), 4.,86 g of vanadium pentoxide, 1.75 g of niobium pentoxide, 1587.96 g of demineralized water and 97.7 g of organic binder (copolymer of vinyl acetate and vinyl laurate in the form of a 50% by weight aqueous dispersion).

After calcination of the catalyst at 450° C. for one hour, the active composition applied to the steatite rings was 9.0%. The analyzed composition of the active material consisted of 7% $V_2O_5$, 0.2% $Nb_2O_5$, 0.92% Cs, remainder $TiO_2$.

Catalyst zone 2 (CZ2): Preparation analogous to CZ1, variation of the composition of the suspension. After calcination of the catalyst at 450° C. for one hour, the active material applied to the steatite rings was 9.1%. The analyzed composition of the active material consisted of 7% $V_2O_5$, 0.2% $Nb_2O_5$, 0.67% Cs, remainder $TiO_2$ with a mean BET surface area of 20 m²/g (Fuji TA 100 C anatase).

Catalyst zone 3 (CZ3): Preparation analogous to CZ1, variation of the composition of the suspension. After calcination of the catalyst at 450° C. for one hour, the active material applied to the steatite rings was 9.0%. The analyzed composition of the active material consisted of 7% $V_2O5$, 0.2% Nb2O5, 0.35% Cs, 0.04% K (introduced into the suspension as sulfate), 0.03% P (introduced into the suspension as dihydrogenphosphate), remainder TiO2 having a mean BET surface area of 22.1 m²/g (mixture of Fuji TA 100 C anatase, BET surface area of 20 m²/g, and Fuji TA 100 CT anatase, BET surface area of 27 m²/g).

Catalyst zone 4 (CZ4): Preparation analogous to CZ1, variation of the composition of the suspension. After calcination of the catalyst at 450° C. for one hour, the active material applied to the steatite rings was 8.0%. The analyzed composition of the active material consisted of 20% V2O5, 0.18% P (introduced into the suspension as dihydrogenphosphate), 0.24% W (introduced into the suspension as WO3), remainder TiO2 having a mean BET surface area of 20 m$^2$/g (Fuji TA 100 C anatase).

Catalytic Oxidation of Naphthalene or of a Mixture of Naphthalene and o-xylene to Phthalic Anhydride on the Model Tube Scale The catalytic oxidation of o-xylene to phthalic anhydride was performed in a salt bath-cooled tubular reactor having an internal diameter of the tubes of 25 mm. From the reactor inlet to the reactor outlet, in each case 80 cm of CZ1, 80 cm of CZ2, 90 cm of CZ3 and 90 cm of CZ4 were introduced into an iron tube of length 3.5 m with an internal width of 25 mm. The iron tube was surrounded by a salt melt for temperature regulation; a 4 mm external diameter thermowell with installed tensile element served for catalyst temperature measurement.

Preforming of the catalysts was effected under 0.1 M$^3$ (STP)/h of air at 400° C. for about 24 hours.

After starting up the catalyst at 380° C., 3.0 to 4.0 M$^3$ (STP) of air per hour flowed through the tube from the top downward with loadings of 97.5% by weight naphthalene or mixtures of 97.5% by weight naphthalene and 99-99.4% by weight o-xylene totaling 30 to 80 g/m$^3$ (STP). The thermal bed temperature (salt bath temperature) was lowered proceeding from 386° C. The PA yields were measured in the reaction outlet gas and are reported in % by mass (kg of PA per kg of naphthalene or naphthalene and o-xylene converted), based on 100% reactant.

Example 8 (INVENTIVE)

The different operating parameters are summarized in the following table:

| Run time [days] | Salt bath temperature [° C.] | Gas stream volume [m$^3$ (STP)/h] | Loading [g/m$^3$ (STP)] | | | Naphthoquinone in the reactor outlet gas [% by wt.] | Phthalide in reactor outlet gas [% by wt.] | PA yield [% by wt.] |
|---|---|---|---|---|---|---|---|---|
| | | | Sum | of which naphthalene | of which o-xylene | | | |
| 96 | 380 | 4 | 40.1 | 40.1 | 0 | 1.86 | 0.00 | 105.6 |
| 120 | 377 | 4 | 40.3 | 40.3 | 0 | 1.95 | 0.00 | 105.8 |
| 192 | 377 | 4 | 45.4 | 40.4 | 5 | 1.58 | 0.01 | 107.5 |
| 240 | 376 | 4 | 45.4 | 40.4 | 5 | 1.71 | 0.01 | 105.7 |
| 264 | 376 | 4 | 45.4 | 40.4 | 5 | 1.61 | 0.01 | 106.0 |

Pausing the lowering of the salt bath temperature leads to a reduction in the level of naphthoquinone, an underoxidation product, and hence to an improved product gas composition.

The invention claimed is:

1. A process for preparing carboxylic acids and/or carboxylic anhydrides by gas phase oxidation of aromatic hydrocarbons selected from the group consisting of benzene, xylenes, naphthalene, toluene, durene, and combinations thereof, the process comprising:

passing a gas stream comprising at least one aromatic hydrocarbon selected from the group consisting of benzene, xylenes, naphthalene, toluene, and durene, and molecular oxygen continuously over a catalyst thermostatted by a heat carrier medium in a reactor, during startup of the reactor, lowering the temperature of the heat carrier medium from a temperature in the range from 380 to 410° C. to a temperature in the range of 340 to 365° C., maintaining the temperature of the heat carrier medium constant by pausing the lowering of the temperature for at least 24 hours during the startup of the reactor, during which neither the loading of the gas stream with hydrocarbons nor the gas stream volume is increased by more than 3%.

2. The process according to claim 1, wherein the temperature of the heat carrier medium is kept constant for at least 48 hours.

3. The process according to claim 1, wherein the loading of the gas stream with hydrocarbons in the period during which the temperature of the heat carrier medium is kept constant is increased by a maximum of 1.5%.

4. The process according to claim 1, wherein the gas stream volume in the period during which the temperature of the heat carrier medium is kept constant is increased by a maximum of 2.5%.

5. The process according to claim 1, wherein the loading of the gas stream with hydrocarbons is increased in the course of startup from 25 to 30 g/m$^3$ (STP) to 70 to 120 g/m$^3$ (STP).

6. The process according to claim 1, wherein phthalic anhydride is prepared from o-xylene and/or naphthalene.

7. The process according to claim 1, wherein the catalytically active material of the catalyst comprises vanadium pentoxide and titanium dioxide.

* * * * *